United States Patent [19]

Bercu

[11] Patent Number: 5,065,748
[45] Date of Patent: * Nov. 19, 1991

[54] METHOD OF DIAGNOSING GROWTH HORMONE DISORDERS EMPLOYING SOMATOSTATIN AND GROWTH HORMONE RELEASING HORMONE

[75] Inventor: Barry B. Bercu, Tampa, Fla.

[73] Assignee: University of South Florida, Tampa, Fla.

[*] Notice: The portion of the term of this patent subsequent to Jul. 4, 2006 has been disclaimed.

[21] Appl. No.: 437,041

[22] Filed: Nov. 14, 1989

[51] Int. Cl.$^5$ .............................. A61B 5/00
[52] U.S. Cl. ................... 128/630; 128/632; 424/9; 604/49
[58] Field of Search ............. 604/49, 51; 128/630, 128/632; 424/9; 514/171; 530/311

[56] References Cited

U.S. PATENT DOCUMENTS

| | | | |
|---|---|---|---|
| 4,230,617 | 10/1980 | Sarantakis | 530/311 |
| 4,261,885 | 4/1981 | Sakakibara et al. | 530/311 |
| 4,410,512 | 10/1983 | Bowers | 514/17 |
| 4,727,041 | 2/1988 | Aroonsakul | 436/8 |
| 4,747,825 | 5/1988 | Linkie et al. | 604/51 |
| 4,844,096 | 7/1989 | Bercu | 128/630 |

OTHER PUBLICATIONS

Barkan et al., "Treatment of Acromegaly with Long-Acting Somatostatin Analog SMS 201-995*", Journal of Clinical Endocrinology and Metabolism, vol, 66, No. 1, pp. 16-23, 1988.

Shi, Y. et al., "Clinical and Biochemical Effects of Incremental Doses of the Long-Acting Somatostatin Analog SMS 201-995 in Ten Acromegalic Patients", Clinical Endocrinology, 32(6), 1990, pp. 695-706.

*Primary Examiner*—C. Fred Rosenbaum
*Assistant Examiner*—Mark O. Polutta
*Attorney, Agent, or Firm*—Joseph C. Mason, Jr.; Ronald E. Smith

[57] ABSTRACT

A patient thought to have a hypoactive pituitary or a pituitary that secretes a normal amount of growth hormone in abnormal patterns is given an intravenous bolus of somatostatin at the beginning of a test period. The bolus is followed by an infusion of somatostatin for a two hour period. The infusion is terminated and an intravenous bolus of growth hormone releasing hormone is then administered. The test is performed during the patient's waking hours and a blood sample is taken every twenty minutes to monitor the amount of growth hormone in the patient's bloodstream. The patient is diagnosed based upon the amount of growth hormone released during the treatment, and the rebound rate of growth hormone secretion after suppression. The somatostatin part of the procedure also has utility in connection with the diagnosis of differing types of gigantism and acromegaly.

16 Claims, No Drawings

METHOD OF DIAGNOSING GROWTH HORMONE DISORDERS EMPLOYING SOMATOSTATIN AND GROWTH HORMONE RELEASING HORMONE

TECHNICAL FIELD

This invention relates, generally, to diagnostic tests having utility in connection with the study of growth hormone disorders. More particularly, this invention is concerned primarily with means for diagnosing two main types of growth hormone disorders. First, it relates to cases where the pituitary is hypoactive, i.e., to cases of growth hormone deficiency. Secondly, it relates to cases where the pituitary releases a normal amount of growth hormone but in abnormal, ineffective patterns. However, the invention also has applications in the diagnosing of gigantism and acromegaly.

BACKGROUND ART

The present inventor has heretofore disclosed and patented (U.S. Pat. No. 4,844,096) a method for diagnosing growth hormone disorders employing somatostatin infusion. That diagnostic procedure includes the infusion of somatostatin into the bloodstream of a sleeping patient, coupled with monitoring the growth hormone content of the patient's blood every twenty minutes during the night. The degree of suppression of growth hormone secretion is monitored, together with the rebound rate of secretion after the infusion is stopped.

That patented procedure represents the prior art most relevant to this disclosure.

An article by G. S. Tannenbaum, published in Vol. 124 of Endocrinology, at pps. 1380-1388 (1989), entitled "Paradoxical Enhancement of Pituitary Growth Hormone (GH) Responsiveness to GH-Releasing Factor in the Face of High Somatostatin Tone" is also of interest because it discusses the interplay of somatostatin and growth hormone releasing factor. Also of interest is an article by J. Devesa and others entitled "Reasons for the Variability in Growth Hormone (GH) Responses to GHRH Challenge: The Endogenous Hypothalmic-Somatotroph Rhythm (HSR)," published in Clinical Endocrinology (1989), pps. 367-377.

DISCLOSURE OF INVENTION

The diagnostic procedure of this invention lasts about five hours and is performed in the daytime during the patient's waking hours. A blood sample is taken every twenty minutes during the test to monitor the concentration of growth hormone in the patient's bloodstream.

About ten minutes after an IV of normal saline has been inserted, an IV bolus of somatostatin is given, followed by a two hour IV infusion of somatostatin. At the completion of two hours the somatostatin infusion is discontinued; about twenty minutes thereafter, an IV bolus of growth hormone releasing hormone is administered, and, as aforesaid, the blood sampling is continued until the end of the test.

Thus, in the initial stage of the diagnostic procedure, secretion of growth hormone b the pituitary gland is effectively shut off by the somatostatin; after a twenty minute time period, a bolus of growth hormone releasing hormone stimulates the pituitary to again begin growth hormone secretion. Different individuals respond in widely different ways to this unique treatment, and thus the responses have substantial diagnostic value.

It is therefore seen that a primary object of this invention is to advance the art of growth hormone disorders diagnosis by employing somatostatin and growth hormone releasing hormone in a unique way.

BEST MODES FOR CARRYING OUT THE INVENTION

After a patient having symptoms of a growth hormone disorder has had a good night's sleep and is completely awake, an IV of normal saline is inserted and a sample of blood is taken to determine the amount of growth hormone in the patient's bloodstream. About ten minutes thereafter, a 3.6 ug/kg dose of somatostatin is administered by IV bolus; this initial dose of somatostatin is then followed by a continuing infusion of somatostatin at the rate of 7.2 ug/kg/hr; another blood sample to determine the growth hormone content of the blood is taken about twenty minutes after the IV bolus is administered. The infusion of somatostatin is continued for two hours, and blood samples are taken at twenty minute intervals to monitor the concentration of growth hormone in the patient's blood.

The somatostatin bolus, followed by the infusion, has been found effective to virtually completely shut off growth hormone secretion by the pituitary. Somatostatin and its chemical equivalents, as is well known, is an inhibitor of growth hormone secretion, and the pituitary secretes growth hormone primarily during periods of sleep; both of these factors result in a virtual shut down of growth hormone secretion during the first two hours of the diagnostic procedure, as will be indicated by the blood samples withdrawn from the patient during that time.

After two hours, the somatostatin infusion is discontinued and twenty minutes thereafter an IV bolus of 1 ug/kg of growth hormone releasing hormone (GHRH, also known as Growth Hormone Releasing Factor (GRF)) is administered. The blood sampling at twenty minute intervals continues for another two and a half hours and the procedure is terminated by withdrawing the IV. The sampling ma occur at more frequent intervals, especially shortly after the GRF injection.

The single dose of growth hormone releasing hormone that is administered after the somatostatin infusion has been completed stimulates the pituitary to release growth hormone. It has been found that individual reactions vary greatly among patients, as indicated by the widely ranging concentrations of growth hormone that appear in the respective patient's bloodstreams after the dose of growth hormone releasing hormone has been administered. The information so obtained provides a valuable diagnostic insight into the nature of the patient's disorder.

Specifically, the information enables the physician to classify the patient into one of two primary classes. The first classification includes patients whose pituitary is hypoactive, i.e., those patients suffering from growth hormone deficiency. The second classification includes patients whose pituitary secretes normal amounts of growth hormone each day, in irregular, ineffective patterns. Individuals in this second classification are generally referred to as suffering from neurosecretory dysfunction.

However, the invention is not limited to studies of individuals having growth hormone deficiencies or other neurosecretory dysfunctions. A modified procedure where the GHRH bolus is deleted has also been found to help classify individuals suffering from gigantism and acromegaly.

Gigantism and acromegaly are the same growth disorders; the former name is applied when it appears in children and the latter name is applied to the disorder in adults. The disorder is sometimes caused by a cancerous tumor known as a pituitary adenoma; accordingly, one form of treatment includes surgical removal of the adenoma. Some individuals continue to exhibit the symptoms of gigantism or acromegaly even after the pituitary adenoma has been removed; the present inventive diagnostic procedure has been found useful in the diagnosis of these individuals. For example, when the above-described procedure, without the GHRH bolus, is performed on a child or adult with gigantism or acromegaly, respectively, who has undergone surgery for removal of a pituitary adenoma, the results of the procedure provide valuable information to the diagnosing and treating physicians. If the growth hormone concentration in the blood is not decreased or substantially not decreased after the somatostatin bolus and infusion, the presence of a residual tumor is indicated. On the other hand, if the growth hormone concentration drops after the somatostatin treatment, then the physician knows that the patient is a good candidate for further treatment involving the injection of drugs that inhibit growth hormone secretion. The bolus of GHRH is not administered when these patients are treated. Moreover, the time period for the infusion of somatostatin may be extended for a few more hours as the physician may deem necessary.

To summarize the best mode for carrying out the invention, Table 1 sets forth the above described diagnostic procedure in protocol form:

TABLE 1

GHRH/Somatostatin Protocol
I. Insert IV of normal saline TO IMED PUMP

| Clocktime | Min | GH |
|---|---|---|
| 0800 | 0 | X |
| 0810 | +10 | X |
| SOMATOSTATIN 3.6 ug/kg I.V. bolus and then 7.2 ug/kg/hr I.V. infusion | | |
| 0830 | +20 | X |
| 0900 | +50 | X |
| 0930 | +80 | X |
| 1010 | +120 | X |
| Discontinue Somatostatin | | |
| 1030 | +140 | X |
| GHRH 1 ug/kg I.V. bolus | | |
| 1035 | +145 | X |
| 1040 | +150 | X |
| 1045 | +155 | X |
| 1100 | +170 | X |
| 1115 | +185 | X |
| 1130 | +200 | X |
| 1145 | +215 | X |
| 1200 | +230 | X |
| 1230 | +260 | X |
| 1300 | +290 | X |

Min. Blood Requirements
GH 1.5 cc clot
TOTAL BLOOD VOLUME: 25.5 ml

In view of this disclosure, those skilled in the art will appreciate the fact that many variations in the above protocol could be instituted, while still following the teachings and suggestions of this important invention. The precise amount of the somatostatin and growth hormone releasing hormone boluses could be changed, for example, as well as the timing of the administration thereof. Similarly, the rate of infusion of somatostatin that follows the somatostatin bolus could be changed as well. Moreover, inhibition of growth hormone secretion could be accomplished by any chemical equivalent of somatostatin. Thus, wherever somatostatin is referred to in this disclosure or the claims appended hereto, it should be understood that its chemical equivalents are also referred to and claimed as a matter of law.

Clearly, the essence of this invention resides in the use both somatostatin and growth hormone releasing hormone as parts of a diagnostic test conducted during the patient's waking hours. The test could also be performed during the patient's sleeping hours, but such a nocturnal test would require hospitalization as distinguished from an outpatient diagnostic study.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A method of diagnosing growth hormone deficiency and neurosecretory dysfunction, comprising the steps of:

inhibiting secretion by the pituitary gland of growth hormone by administering to a patient a predetermined dosage of somatostatin;

following said administration by a continuing administration of somatostatin for a predetermined period of time and discontinuing the administration of the somatostatin at the end of said predetermined period of time;

stimulating secretion by the pituitary gland of growth hormone by administering to the patient a predetermined dosage of growth hormone releasing hormone at a predetermined time after the administration of the somatostatin has been discontinued;

monitoring the concentration of growth hormone in the bloodstream of the individual at predetermined intervals of time throughout the performance of the method; and classifying the individual as having a growth hormone deficiency or a neurosecretory dysfunction based upon the individual's response to the procedure.

2. The method of claim 1, wherein the predetermined dosage somatostatin is administered by an intravenous bolus.

3. The method of claim 2, wherein the predetermined dosage of the somatostatin is 3.6 ug/kg.

4. The method of claim 3, wherein said predetermined dosage of the somatostatin is administered when the patient is awake.

5. The method of claim 4, wherein the administration of the somatostatin bolus is immediately followed by an infusion of somatostatin at a predetermined rate.

6. The method of claim 5, wherein the predetermined rate of somatostatin infusion is 7.2 ug/kg/hr.

7. The method of claim 6, wherein the predetermined period of time for the administration of the somatostatin infusion is two hours.

8. The method of claim 7, wherein said growth hormone releasing hormone is administered twenty minutes after the infusion of somatostatin has been discontinued.

9. The method of claim 8, wherein the affects of the foregoing steps are monitored at twenty minute intervals.

10. A method of determining whether a patient with gigantism or acromegaly is a candidate for a treatment program including the injection of drugs that inhibit the secretion of growth hormone, comprising the steps of:
administering to the patient a predetermined dosage of somatostatin;
following said administration by a continuing administration of said somatostatin for a predetermined period of time;
monitoring the concentration of growth hormone in the bloodstream of the individual at predetermined intervals of time throughout the performance of the method;
classifying the individual as a candidate or a non-candidate for further treatment by drug injection of somatostatin based upon the information gained from said monitoring; and
determining whether or not a residuary tumor is present in those patients who have undergone surgical removal of a pituitary adenoma based upon the information gained from said monitoring.

11. The method of claim 10, wherein the predetermined dosage of somatostatin is administered by an intravenous bolus.

12. The method of claim 11, wherein the predetermined dosage of the somatostatin is 3.6 ug/kg.

13. The method of claim 12, wherein said predetermined dosage of the somatostatin is administered when the patient is awake.

14. The method of claim 13, wherein the administration of the somatostatin bolus is immediately followed by a infusion of somatostatin at a predetermined rate.

15. The method of claim 14, wherein the predetermined rate of somatostatin infusion is 7.2 ug/kg/hr.

16. The method of claim 15, wherein the predetermined period of time for the administration of the somatostatin infusion is two hours.

* * * * *